United States Patent [19]

Sugimoto et al.

[11] 4,061,744

[45] Dec. 6, 1977

[54] STABLE PREPARATION OF WATER-SOLUBLE SALTS OF DEHYDROEPIANDROSTERONE SULFATE FOR PARENTERAL ADMINISTRATION

[75] Inventors: Isao Sugimoto, Nara; Yoko Sawase, Osaka, both of Japan

[73] Assignee: Kanebo, Ltd., Tokyo, Japan

[21] Appl. No.: 719,278

[22] Filed: Aug. 31, 1976

[30] Foreign Application Priority Data

Sept. 5, 1975 Japan .................................. 50-108197
July 6, 1976 Japan .................................. 51-80613

[51] Int. Cl.$^2$ ............................................ A61K 31/56
[52] U.S. Cl. ................................. 424/243; 260/397.4
[58] Field of Search .............................. 424/242, 243

[56] References Cited

U.S. PATENT DOCUMENTS 4,005,200   1/1977   Utsumi et al. ...................... 260/397.5

*Primary Examiner*—Elbert L. Roberts
*Attorney, Agent, or Firm*—Haight & Huard

[57] ABSTRACT

A water-soluble salt of dehydroepiandrosterone sulfate is dissolved in an aqueous solution of a compound selected from the group consisting of dextran, macrogol, a neutral amino acid, a basic amino acid, an alkali metal salt of a weak acid, a solid amine, and mixtures thereof and then the resulting mixture is lyophilized.

The product is stable on storage for a long period of time and easily soluble in water upon use for parenteral administration.

13 Claims, No Drawings

STABLE PREPARATION OF WATER-SOLUBLE SALTS OF DEHYDROEPIANDROSTERONE SULFATE FOR PARENTERAL ADMINISTRATION

This invention relates to a method for producing a stable pharmaceutical preparation of a water-soluble salt of dehydroepiandrosterone sulfate for parenteral administration.

Dehydroepiandrosterone sulfate (hereinafter referred to as "DHA-S") has been known to be a secretional form of steroidal hormones and found in human urine as the sodium salt. DHA-S is formed from free dehydroepiandrosterone in vivo and circulates in the body as DHA-S. A large quantity of DHA-S is secreted by the adrenal glands of a fetus and takes an important part in maintaining normal pregnancy. DHA-S is formed also in the ovary and testes and secreted into body fluids.

Recently it has been discovered that when DHA-S is administered to a pregnant human subject at the 37th to 39th week of pregnancy, it improves maturity of parturient canal and sensibility of uterine musculature to oxytocin, thereby, enhancing safe, normal parturition. Thus the clinical application of DHA-S has become of great importance. Unfortunately water-soluble salts of DHA-S are very unstable in the presence of water. For instance, the sodium salt of DHA-S will be partly hydrolized into free dehydroepiandrosterone when aqueous solutions thereof are stored, even at room temperature, for a short period of time.

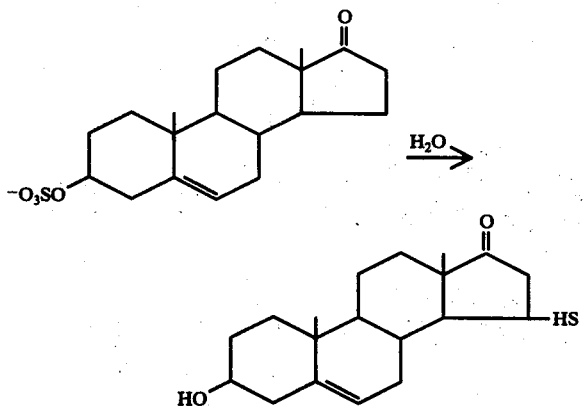

Accordingly its dosage forms must be sterile dry crystals or lyophilized powders packed in a container which are redissolved in sterile water upon each use. The above forms are not satisfactory because the crystals take a long time to dissolve in water upon use and the lyophilized powders do not have sufficient shelf life at room temperature.

According to the present invention, we have found that a stable preparation of a water-soluble DHA-S for parenteral administration may be obtained by dissolving said salt in an aqueous solution containing a compound selected from the group consisting of dextran, polyethylene glycol, a neutral amino acid, a basic amino acid, an alkali metal salt of a weak acid, a solid amine and mixtures thereof, and then lyophilizing the resulting mixture.

The resulting powders are stable for a long period time on storage and may be easily dissolved in sterile water for parenteral administration such as intravenous or intramuscular injections upon use.

The water-soluble salts of DHA-S which can be employed in practicing the invention are alkali metal salts such as sodium salt of potassium salt, ammonium salt, and amine salts such as L-lysine salt or L-arginine salt.

The compounds which can be added in accordance with the present invention are dextran having an average molecular weight from 30,000 to 100,000 such as dextran 40(average M.W.=40,000) and dextran 70(average M.W.=70,000) both Japanese Pharmacopeia, 8th edition(JP); polyethylene glycols such as polyethylene glycols 1,500, JP, polyethylene glycols 4,000, JP and macrogol 6,000,JP; neutral or basic naturally occurring amino acids (D-, L-, or DL- form) such as glycine, alanine, leucine, arginine, histidine, lysine and ornithine; alkali metal salts of weak oganic or inorganic acids such as the sodium and potassium salts of citric, tartaric, succinic, acetic, phosphoric, boric and carbonic acids; and a solid amine such as tris(hydroxymethyl) aminomethane.

The amino acids, the alkali metal salts of weak acids and the solid amines are known to be buffers.

The amount of the stabilizing agents is at least 10%, preferably 20% to 200%, by weight of the water-soluble salt of DHA-S.

It has been found that solubility of DHA-S is remarkably increased by the presence of dextran, macrogol and amino acids.

For example solubility of DHA-S sodium salt in plain water at room temperature is 1.4%, but the solubility in a 2% aqueous solution of glycine is 3.0%. Thus ampoules each containing 100mg. of DHA-S sodium salt are obtained by dispensing 5ml. of the solution in 2% glycine, whereas 10ml. is needed if plain water is used to dissolve the DHA-S sodium salt. This greatly reduces the amount of water to be removed and also the time required for lyophilization.

In practice a water-soluble salt of DHA-S is dissolved in a solution of the stabilizing agent and the solution is sterilized by filtration in a conventional manner. The solution is dispensed in a container such as ampoules or vials and then lyophilized in a conventional manner. The container is finally sealed.

Upon use, the content of the container is re-dissolved by adding a sufficient amount of sterile water therein.

The following examples will illustrate the invention.

EXAMPLE 1

100mg. of DHA-S sodium salt was mixed with various amounts of polyethylene glycol macrogol 4,000, JP. The mixture was dissolved in 5ml. of sterile water. The solution was filled in an ampoule under sterile conditions and then lyophilized. The ampoules were stored at 50° C for 10 days, 20 days and 30 days, respectively and the residual amounts of DHA-S sodium salt were determined. The results obtained are shown in Table 1.

TABLE 1

| Amount of macrogol, mg | Moisture content % | Residual amount of DHA-S Na after storage at 50° C | | | Dissolving time in water, seconds |
|---|---|---|---|---|---|
| | | 10 days | 20 days | 30 days | |
| 0 | 5.2 | 82.9 | 68.8 | 61.1 | 10 |
| 10 | 5.4 | 89.8 | 78.3 | 72.7 | 12 |
| 20 | 5.3 | 93.3 | 92.1 | 90.8 | 11 |
| 50 | 5.5 | 95.5 | 93.2 | 90.1 | 13 |
| 100 | 5.1 | 97.3 | 96.6 | 95.5 | 13 |
| 120 | 5.3 | 96.2 | 95.3 | 95.1 | 16 |
| 150 | 5.4 | 97.1 | 95.8 | 94.9 | 17 |
| 200 | 5.3 | 98.0 | 96.0 | 95.3 | 24 |

It will be understood from Table 1 that DHA-S sodium salt is substantially stabilized by the addition of 20 mg. to 150mg. of macrogol and dissolves within a reasonable length of time within said range.

EXAMPLE 2

The procedure of Example 1 was repeated except that DHA-S L-histidine salt and macrogol 6,000, JP were substituted for DHA-S sodium and macrogol 4,000.

As shown in Table 2 satisfactory results were obtained with 20mg. to 150mg. of macrogol 6,000.

TABLE 2

| Amount of macrogol, mg | Moisture content % | Residual amount of DHA-S Na after storage at 50° C | | | Dissolving time in water, seconds |
|---|---|---|---|---|---|
| | | 10 days | 20 days | 30 days | |
| 0 | 7.1 | 80.6 | 72.2 | 66.3 | 8 |
| 20 | 6.8 | 90.8 | 87.2 | 82.2 | 8 |
| 50 | 7.2 | 93.3 | 88.7 | 85.5 | 9 |
| 100 | 6.9 | 92.3 | 90.1 | 86.7 | 9 |
| 150 | 7.1 | 94.0 | 91.0 | 88.8 | 11 |
| 200 | 7.0 | 93.7 | 90.6 | 87.2 | 15 |

EXAMPLE 3

The procedure of Example 1 was repeated except that dextran 40,JP was substituted for macrogol 4,000.

As shown in Table 3, satisfactory results were obtained with 20mg. to 150mg. of dextran 40.

TABLE 3

| Amount of dextran mg | Moisture content % | Residual amount of DHA-S Na after storage at 50° C | | | Dissolving time in water, seconds |
|---|---|---|---|---|---|
| | | 10 days | 20 days | 30 days | |
| 0 | 4.8 | 83.3 | 70.0 | 63.3 | 11 |
| 10 | 5.0 | 91.1 | 83.3 | 76.6 | 12 |
| 20 | 5.2 | 93.9 | 89.6 | 88.8 | 13 |
| 50 | 4.6 | 94.4 | 93.3 | 91.3 | 13 |
| 100 | 4.9 | 93.8 | 92.6 | 90.7 | 14 |
| 150 | 5.0 | 94.7 | 93.0 | 92.4 | 16 |
| 200 | 5.1 | 93.9 | 91.2 | 90.0 | 20 |

EXAMPLE 4

The procedure of Example 1 was repeated except that a 1:1 mixture of macrogol 4,000, JP and dextran 70, JP was substituted for macrogol 4,000.

As shown in Table 4, satisfactory results were obtained with 20 mg. to 150 mg. of the mixture of macrogol 4,000 and dextran 70.

TABLE 4

| Amount of 1:1 mixture of macrogol 4,000 and dextran 70, mg. | Moisture content, % | Residual amount of DHA-S Na after storage at 50° C | | | Dissolving time in water, seconds |
|---|---|---|---|---|---|
| | | 10 days | 20 days | 30 days | |
| 0 | 6.2 | 83.3 | 73.9 | 66.2 | 12 |
| 20 | 5.7 | 90.3 | 88.3 | 86.6 | 14 |
| 50 | 5.5 | 93.1 | 91.3 | 89.6 | 14 |
| 100 | 6.1 | 94.5 | 92.4 | 88.7 | 16 |
| 150 | 5.8 | 93.8 | 90.8 | 89.6 | 18 |
| 200 | 5.9 | 94.2 | 93.1 | 90.0 | 22 |

EXAMPLE 5

40g. of glycine was dissolved in distilled water in a 2 liter capacity container. To the solution was added 40g. of DHA-S sodium salt with warming. The total volume of the solution was made to 2 liters with distilled water. The solution was sterilized by filtration in a conventional manner and dispensed in 5 ml. each in a glass ampoule. The solution was then lyophilized and sealed in a conventional manner. Each ampoule contained 100mg. of DHA-S sodium and 100mg. of glycine. The above procedure was repeated with various amounts of glycine. Residual amounts of DHA-S sodium salt were determined as Example 1. The results obtained are shown in Table 5.

TABLE 5

| Amount of glycine mg./container | Residual amount of DHA-S Na after storage at 40° C,% | |
|---|---|---|
| | 30 days | 90 days |
| 0 | 78.5 | 58.9 |
| 20 | 95.7 | 94.6 |
| 50 | 98.4 | 97.3 |
| 100 | 99.6 | 98.0 |
| 150 | 98.2 | 97.1 |
| 200 | 99.0 | 98.4 |

EXAMPLE 6

Example 5 was repeated except that L-arginine (free base) was substituted or glycine. Residual amounts of DHA-S sodium salt on the storage test are shown in Table 6.

TABLE 6

| Amount of L-arginine mg./container | Residual amount of DHA-S Na after storage at 40° C, % | |
|---|---|---|
| | 30 days | 90 days |
| 0 | 80.3 | 60.8 |
| 20 | 92.0 | 87.4 |
| 50 | 97.4 | 96.0 |
| 100 | 98.6 | 96.2 |
| 150 | 97.8 | 97.4 |
| 200 | 98.1 | 97.6 |

EXAMPLE 7

Example 5 was repeated except that sodium tartrate was substituted for glycine. Residual amounts of DHA-S sodium salt on the storage test are shown in Table 7.

TABLE 7

| Amount of sodium tartrate, mg/container | Residual amount of DHA-S Na after storage at 40° C, % | |
|---|---|---|
| | 30 days | 90 days |
| 0 | 81.6 | 58.9 |
| 20 | 93.7 | 85.4 |
| 50 | 94.6 | 90.1 |
| 100 | 95.1 | 92.6 |
| 150 | 94.6 | 91.6 |
| 200 | 95.8 | 92.2 |

EXAMPLE 8

Example 5 was repeated except that potassium hydrogen phosphate was substituted for glycine. Residual amounts of DHA-S sodium salt on the storage test are shown in Table 8.

TABLE 8

| Amount of potassium hydrogen phosphate mg/container | Residual amount of DHA-S Na after storage at 40° C, % | |
|---|---|---|
| | 30 days | 90 days |
| 0 | 78.5 | 58.9 |
| 20 | 88.7 | 78.2 |
| 50 | 93.4 | 88.1 |
| 100 | 95.8 | 90.4 |
| 150 | 94.6 | 92.1 |
| 200 | 96.3 | 93.0 |

EXAMPLE 9

Example 5 was repeated except that DL-alanine was substituted for glycine. Residual amounts of DHA-S sodium on the storage test are shown in Table 9.

TABLE 9

| Amount of DL-alanine | Residual amount of DHA-S Na after storage at 40° C, % | |
|---|---|---|
| mg/container | 30 days | 90 days |
| 0 | 77.4 | 55.4 |
| 20 | 85.3 | 82.3 |
| 50 | 91.4 | 87.4 |
| 100 | 95.2 | 90.1 |
| 150 | 95.4 | 93.3 |
| 200 | 94.7 | 93.2 |

EXAMPLE 10

Example 5 was repeated except that tris(hydroxymethyl)aminomethane was substituted for glycine. Residual amounts of DHA-S sodium salt on the storage test are shown in Table 10.

TABLE 10

| Amount of tris (hydroxyaminomethyl)methane | Residual amount of DHA-S Na after storage at 40° C, % | |
|---|---|---|
| mg/container | 30 days | 90 days |
| 0 | 77.9 | 53.2 |
| 20 | 81.4 | 62.9 |
| 50 | 87.6 | 93.0 |
| 100 | 89.9 | 81.6 |
| 150 | 93.3 | 90.1 |
| 200 | 94.1 | 89.9 |

We claim:

1. A method for producing a stable pharmaceutical preparation for parenteral administration which comprises dissolving a water-soluble salt of dehydroepiandrosterone sulfate in an aqueous solution of a stabilizing agent selected from the group consisting of dextran, polyethylene glycol, a neutral or basic naturally occurring amino acid, an alkali metal salt of a weak acid, tris (hydroxymethy) amindethane and mixtures thereof, and lyphilizing the resulting mixture.

2. The method according to claim 1, wherein said stabilizing agent is added at 10% to 200% by weight fo said water-soluble dehydroepiandrosterone sulfate.

3. The method according to claim 1, wherein said stabilizing agent is selected from the group consisting of dextran, polyethylene glycol, a neutral amino acid and a basic amino acid.

4. The method according to claim 1, wherein said mixture is sterile filtered before lyophilization.

5. The method according to claim 1, wherein said salt of dehydroepiandrosterone sulfate is analkali metal salt.

6. The method according to claim 1, wherein said stabilizing agent is glycine.

7. The method according to claim 1, wherein said stabilizing agent is arginine.

8. The method according to claim 1, wherein said stabilizing agent is sodium tartrate.

9. The method according to claim 1, wherein said stabilizing agent is potassium hydrogen phosphate.

10. The method according to claim 1, wherein said stabilizing agent is alanine.

11. The method according to claim 1, wherein said stabilizing agent is tris(hydroxymethyl) aminomethane.

12. The method according to claim 1, wherein said stabilizing agent is dextran.

13. The method according to claim 1, wherein said stabilizing agent is polyethylene glycol.

* * * * *